(12) United States Patent
Bilgic

(10) Patent No.: US 9,242,979 B2
(45) Date of Patent: Jan. 26, 2016

(54) METHODS FOR THE SYNTHESIS OF TIOTROPIUM BROMIDE

(71) Applicant: Mahmut Bilgic, Istanbul (TR)

(72) Inventor: Mahmut Bilgic, Istanbul (TR)

( * ) Notice: Subject to any disclaimer, the term of this patent is extended or adjusted under 35 U.S.C. 154(b) by 0 days.

(21) Appl. No.: 14/605,618

(22) Filed: Jan. 26, 2015

(65) Prior Publication Data

US 2015/0148540 A1 May 28, 2015

Related U.S. Application Data

(60) Division of application No. 13/632,593, filed on Oct. 1, 2012, now Pat. No. 8,957,209, which is a continuation-in-part of application No. PCT/TR2011/000051, filed on Feb. 23, 2011, and a continuation-in-part of application No. PCT/TR2011/000052, filed on Feb. 23, 2011, and a continuation-in-part of application No. PCT/TR2010/000136, filed on Jun. 28, 2010.

(30) Foreign Application Priority Data

| Apr. 1, 2010 | (TR) | ................................. 2010 02520 |
| Jun. 28, 2010 | (TR) | ................................. 2010 05221 |
| Jun. 28, 2010 | (TR) | ................................. 2010 05222 |

(51) Int. Cl.

| C07D 491/08 | (2006.01) |
| A61K 31/44 | (2006.01) |
| C07D 451/00 | (2006.01) |
| C07D 333/24 | (2006.01) |
| C07D 491/18 | (2006.01) |

(52) U.S. Cl.
CPC ............ *C07D 451/00* (2013.01); *C07D 333/24* (2013.01); *C07D 491/18* (2013.01)

(58) Field of Classification Search
None
See application file for complete search history.

(56) References Cited

U.S. PATENT DOCUMENTS

| 6,506,900 B1 | 1/2003 | Banholzer et al. | |
| RE39,820 E * | 9/2007 | Banholzer et al. | ............ 514/291 |
| 2011/0028508 A1 | 2/2011 | Gaitonde et al. | |

FOREIGN PATENT DOCUMENTS

| EP | 0418716 A1 | 3/1991 |
| EP | 1953156 A1 | 8/2008 |
| WO | WO-03057694 A1 | 7/2003 |
| WO | WO-2008089852 A1 | 7/2008 |
| WO | WO-2009087419 A1 | 7/2009 |

OTHER PUBLICATIONS

Melman, A. et al. Selective esterifications of alcohols and phenols through carbodiimide couplings. Org. Biomol. Chem., 2004, vol. 2, p. 399.*

Ishihara, K. et al. Widely Useful DMAP-Catalyzed Esterification under Auxiliary Base- and Solvent-Free Conditions. JACS., 2007, vol. 129, p. 14776.*

(Continued)

*Primary Examiner* — Rita Desai
*Assistant Examiner* — Ben S Michelson
(74) *Attorney, Agent, or Firm* — Clark & Elbing LLP

(57) ABSTRACT

The present invention relates to methods for synthesizing tiotropium bromide following the scheme:

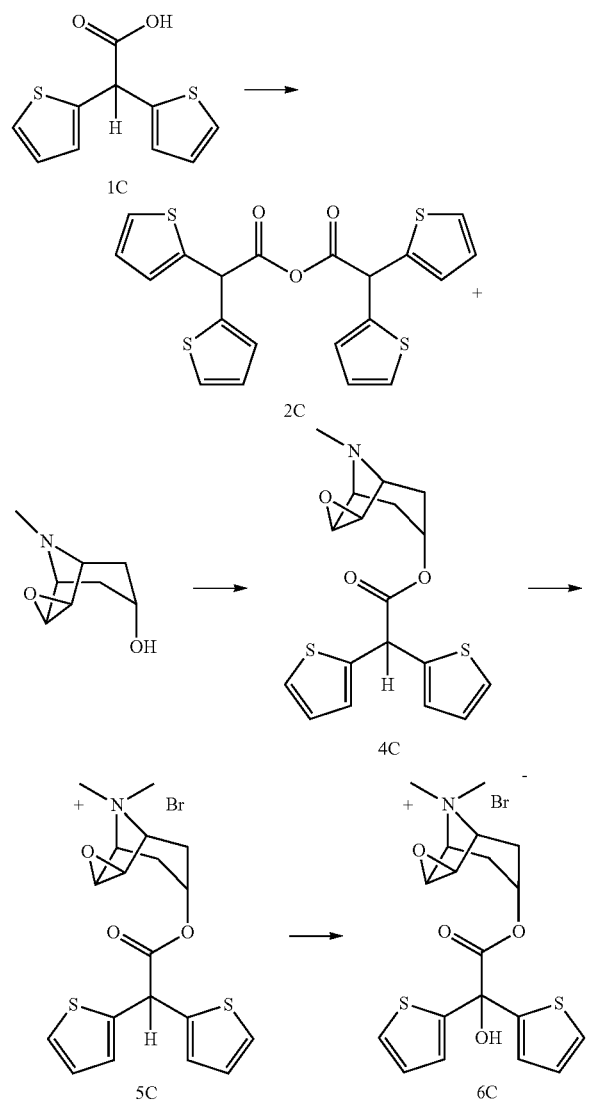

Using the above scheme, tiotropium bromide (compound 6C) is obtained under mild conditions and with high yields.

20 Claims, No Drawings

(56) References Cited

OTHER PUBLICATIONS

Wasserman, HH. et al. Reactions of Lithium Enolates with Molecular Oxygen α-hydroxylation of amides and other carboxylate derivatives. Tetrahedron Letters. 1975, No. 21, p. 1733.*
Sorrell, TN. Organic Chemistry 2nd Edition. University Science Books. 2006, Chapter 15.4, p. 506-509.*
Blicke et al., "Antispasmodics, VIII," J Am Chem Soc. 68(10):1934-6 (1946).
Carey, Chapter 19: Carboxylic Acids. Organic Chemistry 4th Edition. McGraw-Hill College, (2000) (8 pages).
Carey, Chapter 20: Carboxylic Acid Derivatives: Nucleophilic Acyl Substitution. Organic Chemistry 4th Edition. McGraw-Hill College, (2000) (8 pages).
Diafi et al., "8-Hydroxylated derivatives of diazabicyclo[4.3.0]nonanes, 2,5-dioxodiazabicyclo[4.3.0]nonanes and some related esters," J Heterocycl Chem. 27(7):2181-7 (1990).
Examination Report for Turkish Application No. 2010/02520, mailed Sep. 25, 2012 (6 pages).
Search Report for Turkish Application No. 2010/02520, mailed Sep. 20, 2010 (17 pages).
Verdegaal et al., "A convenient synthesis of 2'-$O$-acetal-$N^2$-acyl derivatives of riboguanosin," Recueil des Travaux Chimiques des Pays-Bas. 100(5):200-4 (1981).
Written Opinion and International Search Report for International Application No. PCT/TR2010/000136, mailed Jan. 12, 2011 (10 pages).
Written Opinion and International Search Report for International Application No. PCT/TR2011/000051, mailed Jun. 7, 2011 (10 pages).
Written Opinion and International Search Report for International Application No. PCT/TR2011/000052, mailed Jun. 6, 2011 (10 pages).

* cited by examiner

METHODS FOR THE SYNTHESIS OF TIOTROPIUM BROMIDE

The present invention relates to a new process for preparing (1α, 2β, 4β, 5α, 7β)-7-[(Hydroxidi-2-thienylacetyl)oxy]-9,9-dimethyl-3-oxa-9-azoniatricyclo[3.3.1.0²,⁴]nonane-bromide.

BACKGROUND OF THE INVENTION

The compound whose chemical name is (1α, 2β, 4β, 5α, 7β)-7-[(Hydroxidi-2-thienylacetyl)oxy]-9,9-dimethyl-3-oxa-9-azoniatricyclo[3.3.1.0²,⁴]nonane-bromide is generally known as tiotropium bromide. The compound is shown below with formula 5A and was disclosed for the first time in the patent numbered EP418716.

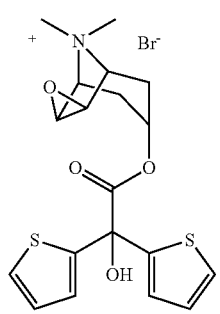

5A

Tiotropium bromide is a highly effective anticholinergic agent and for this reason it is widely used for treatment of asthma and/or COPD (chronic obstructive pulmonary disease).

Tiotropium bromide is generally administered to patients via inhalation. For administration via inhalation, dry powder inhalators wherein the dry powder is filled into blisters/capsules or stored in reservoirs can be used. Another method comprises administration of tiotropium bromide with different gases (e.g. HFA134a and/or HFA227) in aerosol form.

Tiotropyum bromide is a very potent agent and therefore even very small amounts show therapeutic effect.

The patent numbered EP418716 discloses a synthesis method shown in scheme 1 for preparation of tiotropium bromide.

Scheme 1:

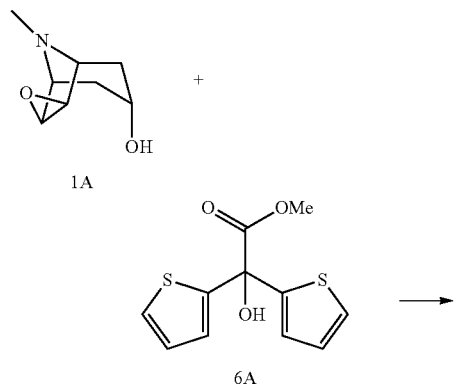

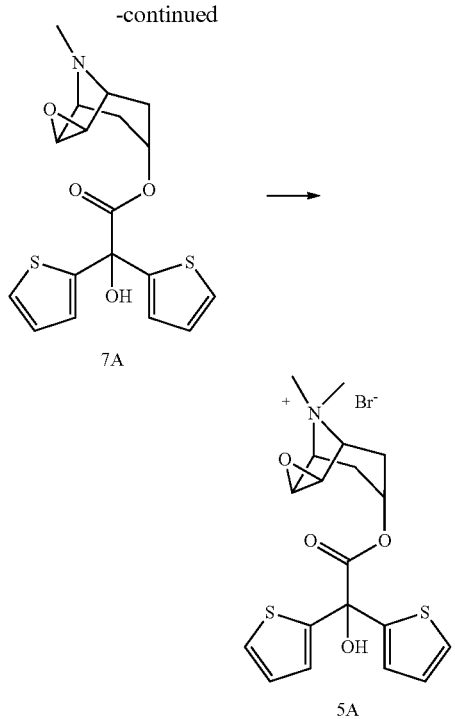

According to this method in the first step scopine that is shown with formula 1A is converted into (2-thienyl)-glycolic acid scopine ester shown with formula 7A by reacting with di-(2-thienyl)-glycolic acid methyl ester that is shown with formula 6A. Afterwards compound of formula 7A is quaternized to give tiotropium bromide.

The first step of this synthesis method is carried out at high temperatures like 70-90° C. and in presence of dangerous chemicals like sodium methoxide and metallic sodium. The fact that the process is carried out at high temperatures increases the cost and makes the process undesirable for the producers. Furthermore although the reactions are carried out under harsh conditions the yields are in the range of 45% and 70% and all of these reasons show that different synthesis methods with higher yields are necessary for preparation of tiotropium bromide.

DETAILED DESCRIPTION OF THE INVENTION

Surprisingly, it was found that, compared to the methods present in prior art, tiotropium bromide was obtained under milder conditions and with higher yields when the synthesis method according to present invention was used. In one aspect, the synthesis method comprises use of the method shown in scheme 2.

Scheme 2:

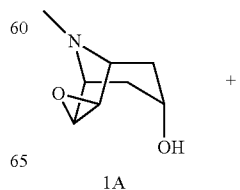

1A

-continued

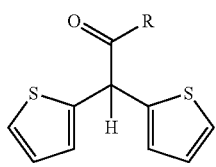

2A

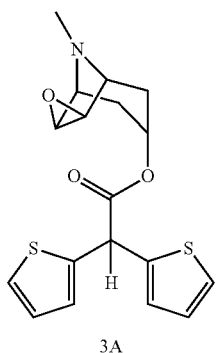

3A

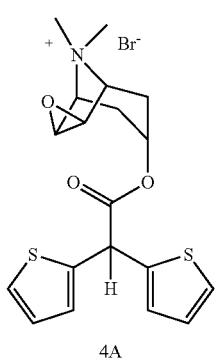

4A

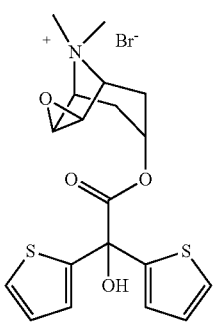

5A

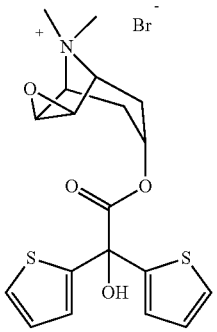

5A conversion of scopine ester shown with formula 3A,

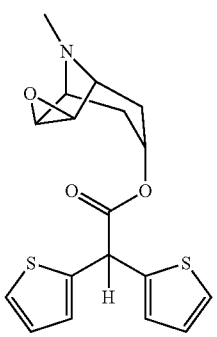

3A into quaternized scopine ester shown with formula 4A

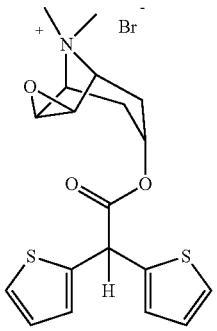

4A and afterwards conversion of formula 4A into the final compound tiotropium bromide (5A).

Another aspect of the present invention is use of scopine ester shown with formula 3 in free base form or in form of its acid addition salts for synthesis of tiotropium bromide (5A)

In another aspect, another important point of the invention is use of scopine ester shown with formula 3A in free form or when necessary in the form of acid addition salts for the preparation of quaternized scopine ester shown with formula 4A. If scopine ester (3A) is used in the form of acid addition salts for producing quartenized scopine ester, this salt can be Upon reaction of scopine or acid addition salts thereof with compound of formula 2A, compound of formula 3A is obtained. Formula 3A is then converted to compound of formula 4A by quatemization. Afterwards an oxidation reaction carried out under appropriate conditions converts compound of formula 4A into the final compound shown with formula 5A which is tiotropium bromide.

In another aspect present invention relates to a synthesis method for preparation of tiotropium bromide (5A) comprising the steps of;

selected from a group comprising hydrochloride, hydrobromide, hydrogenphosphate, hydrogen sulfate, tetrafluoroborate, hexafluorophosphate.

Another aspect of the present invention is related to use of quaternized scopine ester shown with formula 4 for the synthesis of tiotropium bromide (5A).

In another aspect, present invention is related to a process for preparation of tiotropium bromide characterized in that; in the first step scopine or an acid addition salt thereof,

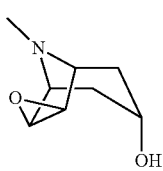

1A is reacted with compound of formula 2A

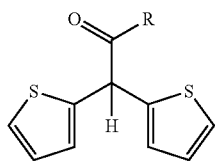

2A wherein, R group in said compound can be chosen from a group comprising hydroxy, methoxy, ethoxy, tertiary butoxide, phenoxy, O—N-succinimide, O—N-phatalimide, phenyloxy, nitrophenyloxy, pentafluorophenyloxy, vinyloxy, —S-methyl, —S-ethyl, —S-phenyl, to give scopine ester shown with formula 3A

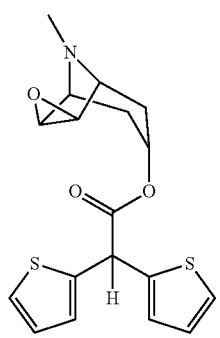

3A and in the second step, compound of formula 3A is quaternized in presence of methyl bromide to give compound of formula 4A

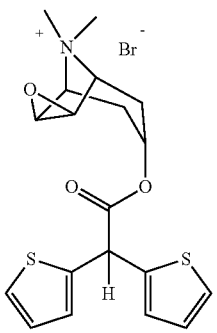

4A and in the third step compound of formula 4A is subjected to an oxidation reaction in presence of organic/inorganic basic compounds in oxygen containing atmosphere to give tiotropium bromide.

Compound of formula 2A which can be used to prepare scopine ester of formula 3A is a compound where R is selected from methoxy, ethoxy, tertiary butoxide, phenoxy, O—N-succinimide, O—N-phatalimide, phenyloxy, nitrophenyloxy, fluorophenyloxy, pentafluorophenyloxy, vinyloxy, —S-methyl, —S-ethyl, —S-phenyl and hydroxy.

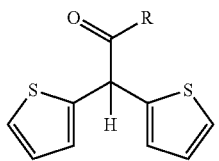

2A

Due to importance of the use of compound of formula 2A in the synthesis of tiotropium bromide as a starting material, another aspect of the present invention relates to use of compound of formula 2A as a starting material for the preparation of tiotropium bromide (5A).

In accordance with the present invention, scopine (1A) can be used in free form or in the form of its acid addition salts such as hydrochloride, hydrobromide, hydrogenphosphate, hydrogensulfate, tetrafluoroborate and hexafluorophosphate. Preferably it is used in free form.

Accordingly a method for preparation of scopine ester shown with formula 3A comprises dissolving scopine in an organic solvent, for example; dimethylformamide (DMF), dimethyl sulfoxide (DMSO), benzene, toluene, diethyl ether, tetrahydrofuran, ethanol, methanol, acetonitrile, acetone, ethyl acetate, methyl ethyl ketone, dichloromethane, dioxane, dimethylacetamide, N-methyl pyrrolidone, hexane, heptane or a mixture of these solvents, preferably dimethylformamide or dichloromethane is used.

If scopine is used in the form of its acid addition salt then a base is added to the solution in order to liberate scopine. According to present invention the base is selected from a group consisting of organic or inorganic bases, for example; from a group comprising triethylamine, diisopropylethylamine, pyridine, dimethylaminopyridine, N-methylpyrolidine, N-methylmorpholine or ammonia. Preferably ammonia is used. Said basic compound is used in an amount of at least 1 mole, preferably in an amount of 1.25 to 2.5 moles, more preferably in an amount of 1.5 to 2.0 moles per 1 mole of scopine used. Addition of the basic compound can take place at a temperature of 0 to 60° C., preferably 15 to 50° C., and more preferably 20 to 30° C. Afterwards the obtained mixture is stirred for 0.5 to 3 hours, more preferably for 1 to 2 hours at a fixed temperature. The salt that forms during the reaction is separated by filtration and the solvent present in the obtained solution is distilled under appropriate heat and pressure. These conditions are determined according to the nature of the solvent used.

The compound obtained is then dissolved in an appropriate organic solvent, for example, dimethylformamide (DMF), dimethyl sulfoxide (DMSO), benzene, toluene, diethyl ether, tetrahydrofuran, ethanol, methanol, acetonitrile, acetone, ethyl acetate, methyl ethyl ketone, dichloromethane, dioxane, dimethylacetamide, N-methyl pyrrolidone, hexane, heptane or a mixture thereof and compound of formula 2A is added to the formed solution.

The compound of formula 2A used in this process is selected from compounds wherein R is selected from a group comprising methoxy, ethoxy, tertiary butoxide, phenoxy, O—N-succinimide, O—N-phatalimide, phenyloxy, nitrophenyloxy, fluorophenyloxy, pentafluorophenyloxy, vinyloxy, —S-methyl, —S-ethyl, —S-phenyl and hydroxy.

If the R group in formula 2A is methoxy, ethoxy, vinyloxy, phenyloxy, —S-methyl, —S-ethyl or —S-phenyl then the reaction is carried out in presence of an organic or inorganic base. As organic base alkali carbonates, or earth alkali carbonates; lithium carbonate, sodium carbonate, potassium carbonate, calcium carbonate, sodium hydride, potassium hydride, calcium hydride, sodium methylate, sodium ethylate, potassium methylate or potassium ethylate can be used. As inorganic base one of the hydrides mentioned above is used. Preferably sodium hydride is used. Said basic compound is added at least in stochiometric amount, preferably in 1 to 3 moles, more preferably 1.5 to 2 moles per mole of scopine. The solution obtained after addition of the base is stirred for 10-120 minutes preferably for 30-90 minutes. If the compound of formula 2A is an ester wherein R is methoxy or ethoxy then the reaction is carried out at a temperature of 40-90° C. preferably at 50-80° C. and more preferably at 60-75° C., under vacuum in order to distill off the alcohol that forms as a side product and thus shift the reaction to the side of the scopine ester.

After completion of the distillation, if necessary, solvent that was also removed during the distillation of the side product can be added again. The obtained solution is then cooled to −5 to 40° C., preferably to 0-35° C., more preferably to 10-25° C. Hydrochloric acid is then added to said solution over 12-120 minutes, preferably over 25-50 minutes. Hydrochloric acid used in this step can be in gaseous form or in form of an aqueous solution; preferably aqueous solution of hydrochloric acid is used. Per one mole of scopine, 80-350 ml, preferably 120-225 ml of 36% hydrochloric acid that is dissolved in 10-20 liters, preferably 12-17 liters of water is added.

After addition of hydrochloric acid solution is complete, the aqueous phase is separated and washed with a water immiscible organic solvent, for example methylene chloride, ethylacetate, toluene, n-butyl acetate, preferably with dichloromethane and then the organic layer is separated and discarded. This step can be repeated if necessary.

The aqueous phase that is obtained is combined with a water immiscible organic solvent, for example; methylene chloride, ethylacetate, toluene, n-butylacetate and an inorganic base, for example carbonates of alkali metals or alkali earth metals for example; lithium carbonate, sodium carbonate, potassium carbonate, calcium carbonate and preferably sodium carbonate is added and pH of the solution is adjusted to 7.5-11, preferably 8-10. Inorganic base is preferably added in the form of its aqueous solution. Accordingly, per mole of scopine, 50-400 g, preferably 100-200 g inorganic base is used by dissolving in 0.25-1.5 L, preferably in 0.5-1.0 L, most preferably in 0.7-0.8 L of water.

After thoroughly mixing the obtained mixture, organic layer is separated. Aqueous phase is washed with a water immiscible organic solvent, for example methylene chloride, ethyl acetate, toluene, n-butylacetate, if necessary this step can be repeated one more time, afterwards organic layers are combined and the organic solvent is removed under appropriate heat and pressure.

The compound obtained after distillation is dissolved in an appropriate solvent, for example dimethylformamide (DMF), dimethyl sulfoxide (DMSO), benzene, toluene, diethyl ether, tetrahydrofuran, ethanol, methanol, acetonitrile, acetone, ethyl acetate, methyl ethyl ketone, dichloromethane, dioxane, dimethylacetamide, N-methyl pyrrolidone, hexane, heptane and a mixture thereof and the obtained solution is heated to the boiling point of the solvent and afterwards slowly cooled to a temperature between −10 to 20° C. Scopine ester that is obtained as a result of this solution is separated by filtration and dried under vacuum.

When R group that is in the compound shown with formula 2A is hydroxy, this compound is shown with formula 2aA;

2aA

The synthesis method for obtaining scopine ester shown with formula 3A comprises the steps of; preparing scopine or an acid addition salt thereof as described before and then dissolving said compound in an appropriate solvent, for example; dimethylformamide (DMF), dimethyl sulfoxide (DMSO), benzene, toluene, diethylether, tetrahydrofuran, ethanol, methanol, acetonitrile, acetone, ethyl acetate, methyl ethyl ketone, dichloromethane, dioxane, dimethylacetamide, N-methyl pyrrolidone, hexane, heptane or a mixture thereof and addition of compound of formula 2A wherein R group is hydroxy to said solution and afterwards adding N,N-dicyclohexylcarbodiimide (DCC) 1-ethyl-3-(3-dimethylaminopropyl)carbodiimide (EDC) or N,N'-diisopropylcarbodiimide and optionally 4-dimethylaminopyridine (DMAP). Said reaction mixture is stirred at a temperature of 0-40° C., preferably at room temperature for 10-48, preferably for 12-18 hours.

In this reaction per one mole of scopine, at least 1 mole, preferably 1.05-3 moles, more preferably 1.1-1.8 moles of DCC, EDC or DCI is used. Optionally, per one mole of scopine at least 0.01 moles, preferably 0.03 to 0.2 moles, more preferably 0.05-0.1 moles of DMAP can be added.

At the end of the reaction if solid particles form, the solution is filtered to remove these solid particles, then the solution obtained is diluted with an appropriate organic solvent, for example; dichloromethane, ethyl acetate, hexane, heptanes, and then extracted with water. After removal of organic phase from water phase, the solvent that is used is removed under appropriate conditions. At this point the conditions, e.g. the temperature and pressure, are determined according to the nature of the solvent that is used.

The obtained compound can be purified with conventional purification methods; for example, crystallization with anti-solvent, crystallization with active carbon, thin layer chromatography (TLC), column chromatography, high pressure liquid chromatography (HPLC), distillation etc. if need be.

A method for preparation of quaternized scopine ester shown with formula 4A comprises, dissolving scopine ester shown with formula 3A and/or acid addition salts thereof and a methyl bromide solution comprising methyl bromide in an amount 10-90%, preferably 30-60% by weight in a suitable organic solvent; for example dimethylformamide (DMF), dimethyl sulfoxide (DMSO), benzene, toluene, diethylether, tetrahydrofuran, ethanol, methanol, acetonitrile, acetone, ethyl acetate, methyl ethyl ketone, dichloromethane, dioxane, dimethylacetamide, N-methyl pyrrolidone, hexane, heptane or a mixture thereof and stifling the formed mixture at a temperature of 0-40° C., preferably at room temperature for 12-90 hours, preferably for 18-72 hours.

Methyl bromide solution is prepared by condensing methyl bromide gas at low temperature and then mixing the obtained methyl bromide with an organic solvent; for example, dimethylformamide (DMF), dimethyl sulfoxide (DMSO), benzene, toluene, diethyl ether, tetrahydrofuran, ethanol, methanol, acetonitrile, acetone, ethyl acetate, methyl ethyl ketone, dichloromethane, dioxane, dimethylacetamide, N-methyl pyrrolidone, hexane, heptane or a mixture thereof. The solution is preferably prepared in acetonitrile.

The compound that is obtained can be purified by one of the conventional purification methods for example; crystallization by anti-solvent, crystallization by use of active carbon, thin layer chromatography (TLC), column chromatography, high pressure liquid chromatography (HPLC), distillation etc.

A process for preparation of tiotropium bromide comprises, dissolving quaternized scopine ester compound shown with formula 4A in an organic solvent, for example dimethylformamide (DMF), dimethyl sulfoxide (DMSO), benzene, toluene, diethyl ether, tetrahydrofuran, ethanol, methanol, acetonitrile, acetone, ethyl acetate, methyl ethyl ketone, dichloromethane, dioxane, dimethylacetamide, N-methyl pyrrolidone, hexane, heptane or a mixture thereof that is saturated with oxygen. Preferably acetonitrile or dichloromethane that is saturated with oxygen is used. Then an inorganic base for example; potassium carbonate, sodium carbonate, potassium hydrogen carbonate, sodium hydrogen carbonate, sodium tert-butoxide, triethylamine is added to the formed solution, the formed mixture is stirred at a temperature of −78 to 70° C., preferably at −30 to 60° C., for 1-72 hours, preferably for 3-48 hours.

The compound that is obtained can be purified by one of the conventional purification methods for example; crystallization by anti-solvent, crystallization by use of active carbon, thin layer chromatography (TLC), column chromatography, high pressure liquid chromatography (HPLC), distillation etc.

The present invention also relates to, new intermediates namely; scopine ester shown with formula 3A and its acid addition salts, for example hydrochloride, hydrobromide, hydrogenphosphate, hydrogen sulphate, tetrafluoroborate, hexafluorophosphate salts

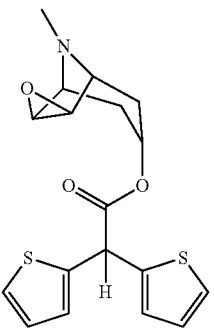

And quaternized scopine ester shown with formula 4A,

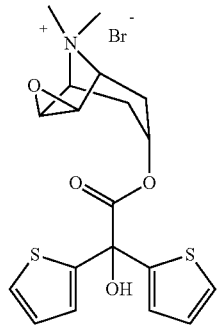

And use of these intermediates for preparation of tiotropium bromide.

The present invention also relates to, pharmaceutical compositions comprising tiotropium bromide prepared according to the present invention and use of said pharmaceutical compositions for the treatment of pulmonary diseases such as asthma, chronic obstructive pulmonary disease (COPD) and allergic rhinitis.

In one aspect, the synthesis method to obtain tiotropium bromide comprises the use of the procedure demonstrated in scheme 3.

Scheme 3:

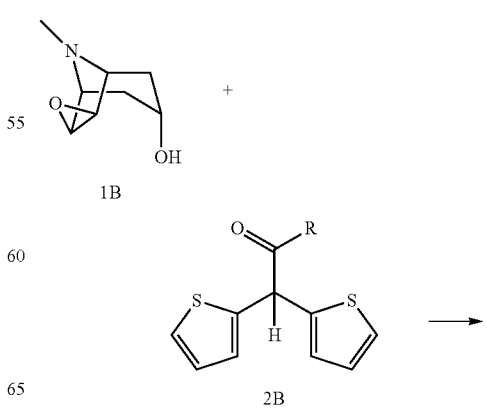

-continued

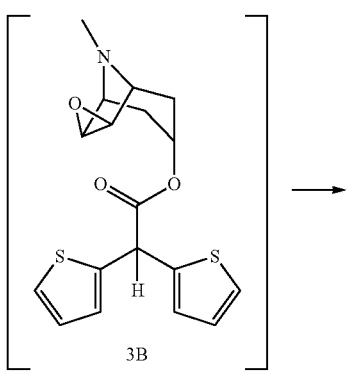
3B

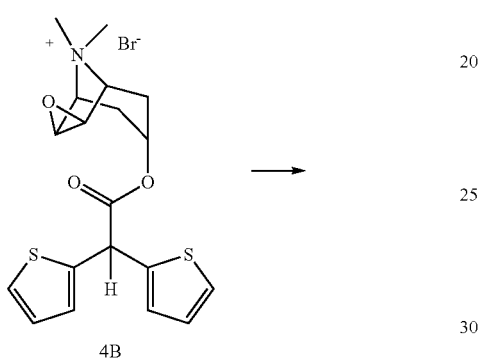
4B

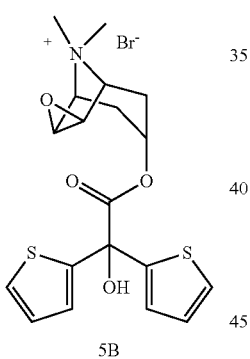
5B

The final product in formula 4B is obtained with higher efficacy and purity when the compound demonstrated in formula 3B is transformed into formula 4B without being isolated.

According to this, one of the constituents of the present invention is the tiotropium bromide synthesis process in which the compound shown in formula 3B that is obtained as a result of the reaction of formula 1B and formula 2B is transformed into formula 4B under convenient conditions without being isolated.

The present invention has decreased the cost of the manufacture by eliminating a purification process that is supposed to be used in the process and managed to obtain formula 4B with higher efficacy.

In one aspect, the present invention relates to a process so as to be used in the synthesis of tiotropium bromide and it comprises the steps of;
a) Obtaining the compound given in formula 3B as a result of the reaction of scopine which is demonstrated in formula 1B or acid addition salts thereof with the compound demonstrated in formula 2B,
b) Transforming the substance, which is obtained after the solid matter in the reaction mixture is removed through filtration, into formula 4B without being subjected to any purification processes,
c) Transforming the quaternized scopine ester demonstrated in formula 4B into tiotropium bromide under convenient oxidation conditions.

According to another aspect, the present invention relates to a method for preparation of tiotropium bromide and comprises the steps that scopine (1B) or an acid addition salt thereof

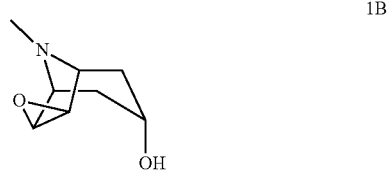
1B and the compound demonstrated in formula 2B,

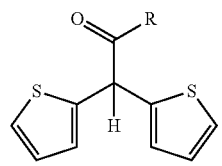
2B wherein the group R in said compound can be selected from a group comprising hydroxy, methoxy, ethoxy, tertiary butoxide, phenoxy, O—N-succinimide, O—N-phthalimide, phenyloxy, nitrophenyloxy, fluorophenyloxy, pentafluorophenyloxy, vinyloxy, —S-methly, —S-ethyl and —S-phenyl, react

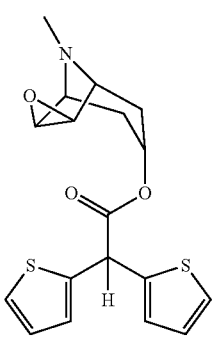
3B and scopine ester demonstrated in formula 3B is obtained at the end of the reaction; the compound illustrated in formula 4B is obtained by quaternizing the substance shown in formula 3B with methyl bromide at the second stage; formula 4B

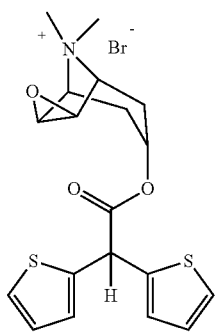
4B is subjected to oxidation reaction in oxygenic environment by using organic and/or inorganic basic substances and the final product tiotropium bromide is obtained at the third stage.

According to the present invention, scopine (1B) can be in free form or in the form of an acid addition salt thereof, for instance hydrochloride, hydrobromide, hydrogenphosphate, hydrogensulphate, tetrafluoroborate and hexafluorophosphate salts. Preferably, it is used in free form.

According to this, the method for the preparation of scopine ester demonstrated in formula 3B requires scopine to dissolve in an appropriate organic solvent, for instance in dimethylformamide (DMF), dimetyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof. Preferably, dimethylformamide or dichloromethane is used.

If scopine is used in the form of its acid addition salt, a base is added in order to reveal scopine. According to the present invention, said base can be selected from a group comprising organic and inorganic bases, for instance from the organic amines triethylamine, diisoprophylethylamine, pyridine, dimethylaminopyridine, N-methylprolidine, N-methyl morphorline or ammoniac. Preferably, ammoniac is used. The amount of said basic substance added is in the range of 1,25-2,5 moles per mole of scopine salt used, preferably in the range of 1,5-2,0 moles per mole of scopine salt used. The basic substance can be added at 0-60° C., preferably at 15-50° C., most preferably at 20-30° C. Following this, the mixture obtained is stirred at constant temperature for 0,5-3 hours, preferably for 1-2 hours. The salt which is produced during the reaction is filtered and removed. The solvent in the obtained solution is distilled under convenient temperature and pressure conditions. These conditions are determined based on the type of the solvent used.

Following this, the substance obtained is dissolved in an appropriate organic solvent, for instance in dimethylformamide (DMF), dimetyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof, and then formula 2B is added.

According to the present invention, the compound of formula 2B to be used here is chosen from a group of compounds wherein R is composed of hydroxy, methoxy, ethoxy, tertiary, butoxide, phenoxy, O—N-succinimide, O—N-phthalimide, phenyloxy, nitrophenyloxy, fluorophenyloxy, vinyloxy, —S-methly, —S-ethyl and hydroxyl.

In the case that R is methoxy, ethoxy, phenyloxy, —S-methly, —S-ethyl or —S-phenyl as formula 2B, the reaction is realized in the presence of a base.

The organic base can be selected from a group comprising alkali carbonates or alkaline earth carbonates, lithium carbonate, sodium carbonate, potassium carbonate, calcium carbonate, sodium hydride, potassium hydride, calcium hydride, sodium methylate, sodium ethylate, potassium methylate and potassium ethylate. As the inorganic base, one of the hydrides is used. Most preferably, sodium hydride is used. The amount of said base used is at least at the stoichiometric proportion, preferably 1-3 moles, most preferably 1,5-2 moles per mole of scopine. The solution which is obtained after the base is added is stirred for 10-120 minutes, preferably for 30-90 minutes. If the formula 2B used is an ester wherein the R it includes is methoxy or ethoxy, the reaction is realized at 40-90° C., preferably at 50-80° C., most preferably at 60-75° C. and preferably under vacuum, and it is provided that the alcohol which is produced as a byproduct during the reaction is distilled and separated. Therefore, the balance of the reaction is readjusted towards scopine ester.

After the distillation is complete, the distilled solvent content of the reaction solution can be added again when necessary. The solution obtained is cooled to 5-40° C., preferably to 0-35° C., most preferably to 10-25° C. after the distillation is finished. The solution at this temperature is added hydrochloric acid for 12-120 minutes, preferably for 25-50 minutes. The hydrochloric acid used here can be in gas or aqueous solution form. However, it is preferred to be in aqueous solution form. Per one mole of scopine used, 80-350 ml of 36% hydrochloric acid, particularly 120-225 ml of 36% hydrochloric acid is added as dissolved in 10-20 liters of water, preferably in 12-17 liters of water.

Subsequent to the addition of hydrochloric acid solution, aqueous phase is separated. It is washed with a water immiscible organic solvent such as methylene chloride, ethyl acetate, toluene, n-butyl acetate, but preferably methylene chloride; organic phase is separated and removed. This step can be repeated if required.

The obtained aqueous phase is mixed with a water immiscible organic solvent such as methylene chloride, ethyl acetate, toluene, n-butyl acetate, and the pH value of the solution is adjusted in the range of 7,5-11, preferably in the range of 8-10 by adding an inorganic base into it, for instance carbonates of alkali metals or alkaline earth metals such as lithium carbonate, sodium carbonate, potassium carbonate, calcium carbonate, most preferably sodium carbonate. The inorganic base is preferably added in the form of aqueous phase. According to this, 50-400 g, preferably 100-200 g of organic base per one mole is used as dissolved in 0,5-1,0 L, particularly preferably in 0,7-0,8 L of water.

After the obtained mixture is stirred, the organic phase is separated. The aqueous phase is extracted with a water immiscible organic solvent such as methylene chloride, ethyl acetate, toluene, n-butyl acetate. This step can be repeated if required. Then, the organic phases are combined and the organic solvent is distilled at an appropriate temperature and pressure to be removed.

The substance obtained upon distillation is dissolved in an appropriate solvent, for instance in a solvent combination which is comprised of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof. The obtained solution is heated up to the boiling point of the solvent used, and then it is slowly cooled to −10-20° C.

Scopine ester which is obtained upon this procedure is filtered from the solution and dried under vacuum.

In the case that the group R in the compound, which is demonstrated in formula 2B, is hydroxy (formula 2aB),

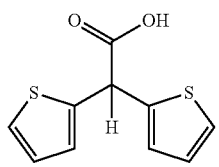

2aB the synthesis method that will be used so as to obtain scopine ester illustrated in formula 3B comprises the steps of preparing scopine and acid addition salt thereof as described above; dissolving it in an appropriate solvent such as dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof; adding the compound wherein the group R is hydroxyl which is demonstrated in formula 2B into the obtained solution; and adding N,N'-dicyclohexylcarbodiimide (DCC), 1-Ethyl-3-(3-dimethylaminopropyl)carbodiimide (EDC) or N,N'-diisopropylcarbodiimide (DIC) and optionally 4-dimethylaminopyridine (DMAP) into the obtained solvent. Said reaction is stirred at −10-40° C., preferably at room temperature for 10-48 hours, preferably for 12-16 hours.

In the said reaction, at least 1 mole, preferably 1,05-3 moles, most preferably 1,1-1,8 moles DCC, EDC or DIC is added per mole of scopine. Optionally, at least 0,01 mole, preferably 0,03-0,2 mole, most preferably 0,05-0,1 mole of DMAP per mole of scopine can be added.

In the case that solid particles remain in the solution at the end of the reaction, the solution is put through filtration. The solution that is obtained after the solid substance is filtered is diluted with an organic solvent, for instance dichloromethane, ethyl acetate, hexane, heptane, and it is extracted with water. After the organic phase is separated from the aqueous phase, the solvent used is removed under convenient conditions. The conditions to be used here, such as temperature and pressure, are chosen in accordance with the type of the solvent used.

Without being subjected to any purification operations, the obtained substance is dissolved in an appropriate organic solvent, for instance in a solvent combination which is comprised of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof and the organic solution which contains 90-10%, preferably 30-60% of methyl bromide by weight is added into it. Then, it is stirred at 0-40° C., preferably at room temperature for 12-90 hours, preferably for 18-72 hours and the quaternized scopine ester that is demonstrated in formula 4B is obtained.

According to another aspect, the present invention comprises the transformation of scopine ester which is demonstrated in formula 3B into quaternized scopine ester which is demonstrated in formula 4B without being subjected to any chromatographic purification processes.

The methyl bromide solution mentioned here is obtained through condensing methyl bromide gas at low temperature, then dissolving it in a desired organic solvent, for instance in a solvent combination which is comprised of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof. Preferably, it is dissolved in acetonitrile solution.

If required, the obtained substance can be purified through one of the conventional purification methods such as anti-solvent crystallization, activated charcoal crystallization, thin layer chromatography (TLC), column chromatography, high pressure liquid chromatography (HPLC), distillation and the methods in the prior art.

The method for the preparation of tiotropium bromide which is illustrated in formula 5B is comprised of the stages of dissolving quaternized scopine ester demonstrated in formula 4B in an oxygen-saturated organic solvent, for example in a solvent that is comprised of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof, preferably in acetonitrile or dichloromethane; adding an organic or an inorganic base such as potassium carbonate, sodium carbonate, potassium hydrogen carbonate, sodium tert-butoxide, triethyl amine into the obtained solvent; and stirring the obtained blend at −78-70° C., preferably at −30-60° C. for 1-72 hours, preferably for 3-48 hours.

Another constituent of the present invention is that tiotropium bromide which is prepared according to the present invention is used in the production of a drug so as to be used in the treatment of many respiratory diseases, especially in asthma, chronic obstructive lung disease (COPD) and allergic rhinitis.

An alternative method for the synthesis of tiotropium bromide (formula 6C)

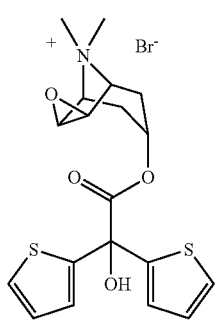

6C comprises that; di-(2-thienyl)-acetic acid shown in formula 1C

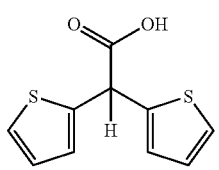

1C is transformed into formula 2C which is a form of acid anhydride;

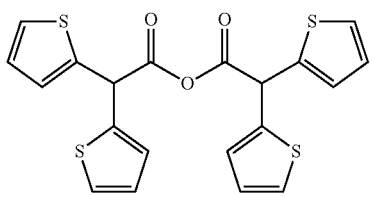

2C scopine ester that is demonstrated in formula 4C is obtained through reacting the obtained acid anhydride with scopine;

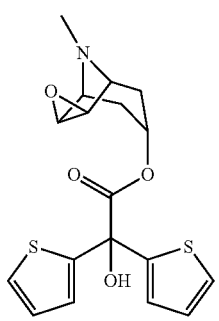

4C the compound shown in formula 5C is obtained upon quaternizing scopine ester with methyl bromide;

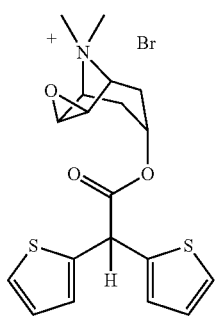

5C the compound obtained at the end is transformed into tiotropium bromide after it is processed with organic and/or inorganic basic substances.

Steiglich esterification, which is a commonly utilized method to synthesize esters by using alcohol and carboxylic acid, comprises the use of a chemical called N,N'-dicyclohexylcarbodiimide (DCC). However, there appears some problems in the purification of the final product obtained since dicyclohexylurea is produced at the end of the reaction as a byproduct of this chemical.

According to this, a method so as to be used in the synthesis of scopine ester shown in formula 4C which is a significant intermediate product for the synthesis of tiotropium bromide

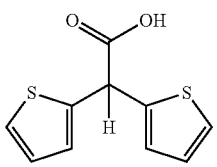

1C comprises the steps of obtaining di-(2-thienyl)-acetic acid anhydride demonstrated in formula 2C through the reaction of di-(2-thienyl)-acetic acid (1) with DCC;

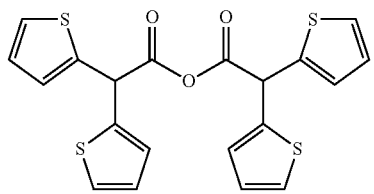

2C then obtaining scopine ester shown in formula 4C through the reaction of the compound demonstrated in formula 2C and scopine with 4-dimethylaminopyridine (DMAP).

The inventors have found that dicyclohexylurea, which is the byproduct of DCC, is eliminated at the previous stage of the synthesis, and therefore purer scopine ester (4C) is obtained.

According to this, the method for the synthesis of di-(2-thienyl)-acetic acid anhydride shown in formula 2C comprises the steps of dissolving di-(2-thienyl)-acetic acid in an appropriate organic solvent such as dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof, most preferably in dichloromethane or dimethylformamide; then adding dicyclohexylcarbodiimide (DCC) into the obtained solution; and stirring it at 0-40° C., preferably at room temperature for 10-48 hours preferably for 12-18 hours.

In said reaction, the amount of DCC added per mole of di-(2-thienyl)-acetic acid used is at least 0,5 mole, preferably in the range of 0,55-3 moles, most preferably in the range of 0,6-1,5 moles.

The solid precipitate which comes out at the end of the reaction is separated through filtration and the solvent in the solution, which is obtained after the solid substance is separated, is removed under convenient conditions. The conditions to be used here, such as temperature and pressure, are determined according to the type of the solvent used.

Another constituent of the invention is to develop a new synthesis method for the preparation of scopine ester shown in formula 4C.

According to this, the method for the preparation of scopine ester shown in formula 4C comprises the steps of dissolving scopine and di-(2-thienyl)-acetic acid anhydride in an appropriate organic solvent such as dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof, most preferably in dichloromethane or dimethylformamide; then adding DMAP into the obtained solution; and stifling it at 0-40° C., preferably at room temperature for 10-48 hours preferably for 12-18 hours.

In said reaction, the amount of di-(2-thienyl)-acetic acid anhydride used per mole of scopine used is at least 1 mole, preferably in the range of 1,05-4 moles, most preferably in the range of 1,1-3,0 moles.

In said reaction, the amount of DMAP added per mole of scopine used is at least 0,05 mole, preferably in the range of 0,1-2,0 moles, most preferably in the range of 0,3-1,0 mole.

After the reaction, the amount of distilled water added into the mixture per mole of di-(2-thienyl)-acetic acid anhydride is at least 0,01 mole, preferably in the range of 0,02-0,2 mole, most preferably in the range of 0,05-0,1 mole. After the distilled water is added, the mixture is stirred at room temperature for 2 hours.

The obtained reaction mixture is diluted by an appropriate organic solvent, for example by DMF, DMSO, benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof, most preferably by dichloromethane or dimethylformamide; and it is extracted with aqueous solutions 1M NaHSO$_4$, 10% Na$_2$CO$_3$ and saturated NaCl respectively. The accumulated solvent layer is dried with and anhydrous Na$_2$SO$_4$ filtered. The organic solvent in the solution obtained is removed under convenient temperature and pressure. The conditions to be used here are determined according to the type of the solvent used.

If required, the obtained substance can be purified through one of the conventional purification methods such as antisolvent crystallization, activated charcoal crystallization, thin layer chromatography (TLC), column chromatography, high pressure liquid chromatography (HPLC), distillation and the methods in the prior art.

The method for the preparation of quaternized scopine ester which is illustrated in formula 5C is comprised of the stages of dissolving scopine ester demonstrated in formula 4C and the organic solution which contains 10-90%, preferably 30-60% methylbromide in an appropriate solvent, for example in a solvent that is comprised of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof, and stirring the obtained mixture at 0-40° C., preferably at room temperature for 12-90 hours, preferably for 18-72 hours.

The methyl bromide solution mentioned here is obtained through condensing methyl bromide gas at low temperature, then dissolving it in a desired organic solvent, for instance in a solvent combination which is comprised of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof. Preferably, it is dissolved in acetonitrile solution.

If required, the obtained substance can be purified through one of the conventional purification methods such as antisolvent crystallization, activated charcoal crystallization, thin layer chromatography (TLC), column chromatography, high pressure liquid chromatography (HPLC), distillation and the methods in the prior art.

The method for the preparation of tiotropium bromide which is illustrated in formula 6C is comprised of the stages of dissolving quaternized scopine ester demonstrated in formula 5C in an oxygen-saturated organic solvent, for example in a solvent that is comprised of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or a combination thereof, preferably in acetonitrile or dichloromethane; adding an organic or an inorganic base such as potassium carbonate, sodium carbonate, potassium hydrogen carbonate, sodium tert-butoxide, triethyl amine into the obtained solvent; and stirring the obtained mixture at −78-70° C., preferably at −30-60° C. for 1-72 hours, preferably for 3-48 hours.

If required, the obtained substance can be purified through one of the conventional purification methods such as antisolvent crystallization, activated charcoal crystallization, thin layer chromatography (TLC), column chromatography, high pressure liquid chromatography (HPLC), distillation and the methods in the prior art.

According to another aspect, the present invention comprises di-(2-thienyl)-acetic acid anhydride shown in formula 2C

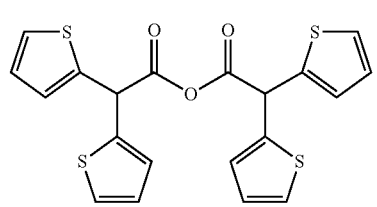

2C and the use of this substance in the synthesis of tiotropium bromide.

EXAMPLES

The examples below are given to explain the subject-matter synthesis method, and the present invention should not be limited with these examples.

Example 1

A Process for Preparation of Scopine Ester (3A)

Scopine (155.2 g, 1 mole) and di-(2-thienyl) acetic acid (246.4 g, 1.1 moles) are dissolved in dichlorometane (700 ml). DCC (268.2 g, 1.3 moles) and DMAP (49 g, 0.4 moles) are then added to the obtained solution and the mixture is then stirred at room temperature for 16 hours. The solid by-product is filtered off and the obtained clear solution is concentrated under low pressure. The crude product is then purified by column chromatography to give 274.4 g of scopine ester (3) (76% yield).

Example 2

A Process for Preparation of Scopine Ester (3A)

Scopine (7.8 g, 0.05 moles) and di-(2-thienyl) acetic acid (12.3 g, 0.055 moles) are dissolved in dichloromethane (80 ml). DCC (15.5 g, 0.075 moles) is then added to the obtained solution and the mixture is stirred at room temperature for 16 hours. The solid by-product is filtered off. The solution is then diluted with dichloromethane (20 ml) and extracted with distilled water (50 ml×3). The organic layer is separated and dried with anhydrous $Na_2SO_4$ and filtered. The obtained clear solution is concentrated under low pressure. The crude product is then purified by column chromatography to give 14.4 g of scopine ester (3A) (80% yield)

Example 3

A Process for Preparation of Scopine Ester (3A)

Scopine (11.6 g, 0.075 moles) and di-(2-thienyl) acetic acid (20.2 g, 0.09 moles) are dissolved in dimethylformamide (50 ml). EDC (14.0 g, 0.09 moles) is then added to the obtained solution and the mixture is stirred for 16 hours at room temperature. The organic solvent is then removed under reduced pressure at a temperature of 50° C. The obtained product is then diluted with dichloromethane (100 ml) and extracted with distilled water (100 ml×3). The organic phase obtained at the end of the extraction process is separated and then dried with anhydrous $Na_2SO_4$ and filtered. The organic solvent is then removed under reduced pressure to give 19.5 g of scopine ester (3A) (72% yield).

Example 4

A Process for Preparation of Scopine Ester (3A)

Scopine (15.5 g, 0.1 moles) and di-(2-thienyl) acetic acid (24.6 g, 0.11 moles) are dissolved in dichloromethane (100 ml). EDC (17.1 g, 0.11 moles) and DMAP (1.2 g, 0.01 moles) are then added to the obtained solution and the mixture is stirred at room temperature for 16 hours.

The obtained product is extracted with distilled water (50 ml×3). At the end of extraction process organic phase is separated and dried with anhydrous $Na_2SO_4$ and then filtered. Organic solvent is then removed under reduced pressure to give 30.0 g of scopine ester (3A) (83% yield).

Example 5

A Process for Preparation of Scopine Ester (3A)

Scopine (1.4 g, 0.009 moles) and di-(2-thienyl) acetic acid (2.2 g, 0.010 moles) are dissolved in dichloromethane (20 ml). DCC (2.04 g, 0.010 moles) is then added to the obtained solution and the mixture is stirred at room temperature for 16 hours. The solid by-product is removed by filtration. The organic solvent is removed under reduced pressure. The crude product is then purified by column chromatography to give 1.95 g of scopine ester (3A) (60% yield).

Example 6

A Process for Preparation of Quaternized Scopine Ester (4A)

Scopine ester (3A) (0.8 g, 0.0022 moles) and acetonitrile solution of methyl bromide (50% wt/wt) (1 ml) are dissolved in acetonitrile and the mixture is the stirred at room temperature for 72 hours. The solid precipitate is then filtered, washed with a suitable solvent and dried under low pressure to give 941 mg of quaternized scopine ester (4A) (94% yield).

Example 7

Process for Preparation of Quaternized Scopine Ester (4A)

Scopine ester (3) (0.8 g, 0.0022 moles) and acetonitrile solution of methyl bromide (50% wt/wt) (1 ml) is dissolved in acetonitrile (1 ml) and the obtained mixture is stirred at room temperature for 24 hours. The formed solid precipitate is then filtered and washed with a suitable solvent, e.g. acetonitrile and dried under vacuum to give 981 mg of quaternized scopine ester (4A) (98% yield).

Example 8

Process for Preparation of Tiotropium Bromide (5A)

Quaternized scopine ester (4A) (0.6 g, 1.32 mmol) and triethylamine (0.36 mL) are dissolved in acetonitrile (12 mL) that is saturated with oxygen gas. The obtained mixture is then stirred at room temperature for 48 hours. The precipitate that forms is then filtrated and the solid is washed with a suitable solvent e.g. acetonitrile, and dried under vacuum to give 460 mg of tiotropium bromide (74% yield).

Example 9

Process for the Preparation of Quaternized Scopine Ester (4B)

Scopine and di-(2-thienyl) acetic acid are dissolved in dichloromethane. The obtained solution is added DCC and the mixture is stirred at room temperature for 16 hours. The solid substance in the reaction mixture is removed through filtration. The solvent in the obtained solution is removed under low pressure. The raw material obtained is dissolved in acetonitrile and added methyl bromide solution (50% MeBr, in acetonitrile). The tube containing the reaction mixture is closed and the obtained mixture is stirred at room temperature for 72 hours. The solid precipitate which comes out at the end is filtered, washed with a solvent, dried under low pressure and quartenized scopine ester (4B) is obtained (80% efficacy).

Example 10

Process for the Preparation of Quaternized Scopine Ester (4B)

Scopine and di-(2-thienyl) acetic acid are dissolved in dichloromethane and cooled to −10° C. The solution prepared by dissolving DDC in dichloromethane is added to this mixture via a syringe, and then the reaction mixture is stirred at room temperature for 12 hours. The solid substance in the reaction mixture is removed through filtration and the solvent is removed under low pressure. The raw material obtained is dissolved in acetonitrile and added methyl bromide solution (50% MeBr, in acetonitrile). The tube containing the reaction mixture is closed and the obtained mixture is stirred at room temperature for 72 hours. The solid precipitate which comes out at the end is filtered, washed with a solvent, dried under low pressure and quartenized scopine ester (4B) is obtained (76% efficacy).

Example 11

Process for the Preparation of Tiotropium Bromide (5B)

Quaternized scopine ester (4B) and an organic base are dissolved in oxygene-saturated acetonitrile and the obtained mixture is stirred at room temperature for 48 hours. The solid precipitate which comes out at the end is filtered, washed with an appropriate solvent such as acetonitrile, dried under low pressure and tiotropium bromide (5B) is obtained (74% efficacy).

Example 12

Process for the Preparation of Di-(2-Thienyl)-Acetic Acid Anhydride (2C)

Di-(2-thienyl)-acetic acid (1C) is dissolved in anhydrous $CH_2Cl_2$, the obtained mixture is added DCC and stirred for 24 hours at room temperature. The solid precipitate which comes out at the end is filtered and separated. The solvent in the obtained solution is removed at room temperature and under low pressure, and di-(2-thienyl)-acetic acid anhydride (2C) is obtained (78% efficacy).

Example 13

Process for the Preparation of Scopine Ester (4C)

Di-(2-thienyl)-acetic acid anhydride (2C) and scopine are dissolved in anhydrous $CH_2Cl_2$, the obtained mixture is added DMAP and stirred for 24 hours at room temperature. Distilled water is added into the reaction mixture and it is stirred for 2 hours at room temperature. The obtained mixture is first diluted with $CH_2Cl_2$, then extracted with aqueous solutions 1M $NaHSO_4$, 10% $Na_2CO_3$ and saturated NaCl respectively. The organic part is separated and dried with anhydrous $Na_2SO_4$. $CH_2Cl_2$ in the solution obtained is removed under low pressure at room temperature. The obtained substance is purified through column chromatography and scopine ester (4C) is obtained (84% efficacy).

Example 14

Process for the Preparation of Quaternized Scopine Ester (5C)

Scopine ester (4C) and acetonitrile solution which comprises 50% of methyl bromide are dissolved in acetonitrile, and the obtained mixture is stirred for 72 hours at room temperature. The solid precipitate which comes out at the end is filtered, washed with an appropriate solvent, dried under low pressure and quartenized scopine ester (5C) is obtained (94% efficacy).

Example 15

Process for the Preparation of Tiotropium Bromide (6C)

Quaternized scopine ester (5C) and an organic base are dissolved in oxygen-saturated acetonitrile and the obtained mixture is stirred at room temperature for 48 hours. The solid precipitate which comes out at the end is filtered, washed with an appropriate solvent such as acetonitrile, dried under low pressure and tiotropium bromide (6C) is obtained (74% efficacy).

The invention claimed is:
1. A synthesis method for preparation of tiotropium bromide, said method comprising:
    a) transforming compound 1C (di-(2-thienyl) acetic acid)

under conditions suitable for anhydride formation to obtain compound 2C (di-(2-thienyl)-acetic acid anhydride);

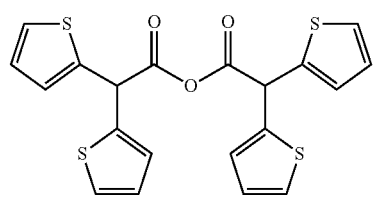

b) reacting compound 2C with scopine to obtain compound 4C;

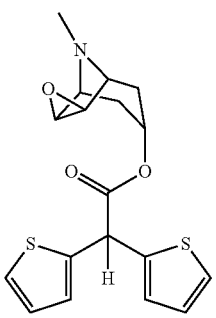

c) converting compound 4C to compound 5C under conditions that do not require a purification procedure; and;

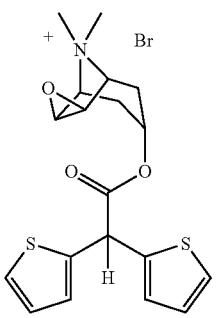

d) oxidizing compound 5C to produce compound 6C

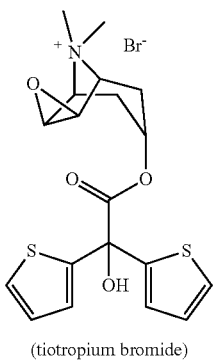

6C (tiotropium bromide)

2. The method of claim 1, wherein step a) comprises
i) dissolving compound 1C in an organic solvent to form a solution;
ii) adding N,N'-dicyclohexylcarbodiimide (DCC) into the solution; and
iii) stirring the solution at a temperature range from 0-40° C. for 10-48 hours.

3. The method of claim 1, wherein step c) comprises
i) dissolving compound 4C in a solution containing from 10-90% methylbromide in an organic solvent; and
ii.) stirring the solution at a temperature range from 0-40° C. for 12-90 hours.

4. The method of claim 1, wherein step d) comprises
i) dissolving compound 5C in an oxygen-saturated organic solvent;
ii) adding an organic or inorganic base into the solution; and
iii) stirring the solution at a temperature range from −78-70° C. for 1-72 hours.

5. The method of claim 1, wherein step b) comprises
i) dissolving scopine and compound 2C in an organic solvent to form a solution;
ii) adding 4-dimethylaminopyridine (DMAP) into the solution; and
iii) stirring the solution at a temperature range from 0-40° C. for 10-48 hours.

6. The method of claim 2, wherein the organic solvent is selected from the group consisting of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or combinations thereof.

7. The method of claim 6, wherein the organic solvent is dicloromethane or dimethylformamide.

8. The method of claim 2, wherein the solution is stirred at room temperature for 12-18 hours.

9. The method of claim 2, wherein the amount of DCC added per mole of compound 1C is in the range of 0.55-3 moles.

10. The method of claim 9, wherein the amount of DCC added per mole of compound 1C is in the range of 0.6-1.5 moles.

11. The method of claim 3, wherein the solution contains 30-60% methylbromide in an organic solvent.

12. The method of claim 3, wherein the organic solvent is selected from the group consisting of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or combinations thereof.

13. The method of claim 3, wherein the solution is stirred at room temperature for 18-72 hours.

14. The method of claim 4, wherein the organic solvent is selected from the group consisting of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or combinations thereof.

15. The method of claim 14, wherein the organic solvent is acetonitrile or dicloromethane.

16. The method of claim 4, wherein the organic or the inorganic base is selected from the group consisting of potassium carbonate, sodium carbonate, potassium hydrogen carbonate, sodium tert-butoxide, and triethyl amine.

17. The method of claim 4, wherein the solution is stirred at a temperature range from −30-60° C. for 3-48 hours.

18. The method of claim 5, wherein the organic solvent is selected from the group consisting of dimethylformamide (DMF), dimethyl sulfoxide (DMSO), benzene, toluene, diethyl ether, tetrahydrofurane, ethanol, methanol, acetonitrile, acetone, ethyl acetate, methyl ethyl ketone, dichloromethane, dioxane, dimethylacetamide, N-methyl pyrrolidone, hexane, heptane or combinations thereof.

19. The method of claim 5, wherein the amount of compound 2C used per mole of scopine is in the range of 1.05-4 moles.

20. The method of claim 5, wherein the amount of DMAP added per mole of scopine is in the range of 0.1-2.0 moles.

* * * * *